United States Patent [19]
Batich et al.

[11] Patent Number: 5,554,147
[45] Date of Patent: Sep. 10, 1996

[54] COMPOSITIONS AND DEVICES FOR CONTROLLED RELEASE OF ACTIVE INGREDIENTS

[75] Inventors: Christopher D. Batich; Marc S. Cohen, both of Gainesville, Fla.; Kirk Foster, Baltimore, Md.

[73] Assignee: CApHCO, Inc., Gainesville, Fla.

[21] Appl. No.: 189,854

[22] Filed: Feb. 1, 1994

[51] Int. Cl.$^6$ ................................................. A61K 9/22
[52] U.S. Cl. .................. 604/890.1; 604/265; 604/891.1; 424/423
[58] Field of Search .............................. 604/890.1, 891.1, 604/892.1, 205, 904, 11

[56] References Cited

U.S. PATENT DOCUMENTS

| | | | |
|---|---|---|---|
| 3,067,745 | 12/1962 | Burgeni | 604/904 |
| 3,861,396 | 1/1975 | Vaillancourt | 604/265 |
| 4,743,248 | 5/1988 | Barton et al. | 604/892.1 |
| 4,999,210 | 3/1991 | Solomon et al. | |
| 5,120,548 | 6/1992 | McClelland et al. | 424/473 |
| 5,152,758 | 10/1992 | Kaetsu et al. | 604/89.01 |
| 5,165,952 | 11/1992 | Solomon et al. | 604/265 |
| 5,217,493 | 6/1993 | Raad et al. | 604/265 |
| 5,261,896 | 11/1993 | Conway et al. | 604/265 |

FOREIGN PATENT DOCUMENTS

| | | |
|---|---|---|
| 0065884 | 12/1982 | European Pat. Off. . |
| 0426486 | 5/1991 | European Pat. Off. . |

OTHER PUBLICATIONS

The Merck Index, 10th edition, 1983, pp. 946–947.

Brazzini, A. et al. (1987) "Urostent Designs" Seminars in Interventional Radiology 4(1):26–34.

Reid, G. et al. (1993) "Adsorption of ciprofloxacin to urinary catheters and effect on subsequent bacterial adhesion and survival" Colloids and Surfaces B:Biointerfaces 1:9–16.

Ritger, P. L., N. A. Peppas (1987) "A Simple Equation for Decsription of Solute Release II. Fickian and Anomalous Release from Swellable Devices" Journal of Controlled Release 5:37–42.

Solomon, D. D., R. J. Sherertz (1987) "Antibiotic Releasing Polymers" Journal of Controlled Release 6:343–352.

Korsmeyer, R. W., N. A. Peppas (1984) "Solute and Penetrant Diffusion in Swellable Polymers. III. Drug Release from Glassy Poly (HEMA–co–NVP) Copolymers" Journal of Controlled Release 1:89–98.

Brannon–Pappas, L., N. A. Pappas (1989) "Solute and Penetrant Diffusion in Swellable Polymers. IX. The Mechanisms of Drug Release from ph–Sensitive Swelling–Controlled Systems" Journal of Controlled Release 8:267–274.

(List continued on next page.)

Primary Examiner—C. Fred Rosenbaum
Assistant Examiner—Chalin Smith
Attorney, Agent, or Firm—Saliwanchik & Saliwanchik

[57] ABSTRACT

A method for the controlled release of a biologically active agent wherein the agent is released from a hydrophobic, pH-sensitive polymer matrix is disclosed and claimed. The polymer matrix swells when the environment reaches pH 8.5, releasing the active agent. A polymer of hydrophobic and weakly acidic comonomers is disclosed for use in the controlled release system. Further disclosed is a specific embodiment in which the controlled release system may be used. The pH-sensitive polymer is coated onto a latex catheter used in ureteral catheterization. A common problem with catheterized patients is the infection of the urinary tract with urease-producing bacteria. In addition to the irritation caused by the presence of the bacteria, urease produced by these bacteria degrade urea in the urine, forming carbon dioxide and ammonia. The ammonia causes an increase in the pH of the urine. Minerals in the urine begin to precipitate at this high pH, forming encrustations which complicate the functioning of the catheter. A ureteral catheter coated with a pH-sensitive polymer having an antibiotic or urease inhibitor trapped within its matrix will release the active agent when exposed to the high pH urine as the polymer gel swells. Such release can be made slow enough so that the drug remains at significant levels for a clinically useful period of time.

8 Claims, 6 Drawing Sheets

OTHER PUBLICATIONS

Franco, G. et al. (1990) "The Incidence of Post-operative Urinary Tract Infection in Patients with Ureteric Stents" British Journal of Urology 65:10–12.

Stamm, W. E. (1991) "Catheter–Associated Urinary Tract Infections: Epidemiology, Pathogenesis, and Prevention" The American Journal of Medicine 91 (suppl 3B):65S–71S.

Nickel, J. C., et al. (1992) "Movement of Pseudomonas Aeruginosa Along Catheter Surfaces" Urology 39(1):93–98.

Swartz, R. et al. (1991) "Biofilm Formation on Peritoneal Catheters Does Not Require the Presence of Infection" Trans. Am. Soc. Artif. Intern. Organs 37:626–634.

McLean R. J. C. et al. (1991) "Pyrophosphate inhibition of *Proteus mirabilis*–induced struvite crystallization in vitro" Clinica Chimica Acta. 200:107–118.

Olson, M. E. et al. (1989) "Animal Model of Human Disease" American Journal of Pathology 135(3):581–583.

McLean, R. J. C. et al. (1990) "Influence of Chondroitin Sulfate, Heparin Sulfate, and Citrate on Proteus Mirabilis–Induced Struvite Crystallization In Vitro" The Journal of Urology 144(1267–1271.

Liedberg, H. et al. (1990) "Refinements in the Coating of Urethral Catheters Reduces the Incidence of Catheter–Associated Bacteriuria" Eur. Urol. 17:236–240.

Breitenbach, J. M., R. P. Hausinger (1988) "*Proteus mirabilis* urease" Biochem. J. 250:917–920.

Takeuchi, H. et al. (1980) "Prevention of Infected Urinary Stones in Rats by Urease Inhibitor" Investigative Urology 18;102–105.

Pearce, R. S. C. et al. (1984) "Evaluation of a New Hydrogel Coating for Drainage Tubes" The American Journal of Surgery 148:687–691.

Ramsay, J. W. A. et al. (1986) "An Experimental Study of Hydrophilic Plastics for Urological Use" British Journal of Urology 58:70–74.

Mardis, H. K., R. M. Kroeger (1988) "Ureteral Stents" Urologic Clinics of North America 15(3):471–479.

acrylic acid diethyleneglycol dimethacrylate methyl methacrylate

COMPOSITIONS AND DEVICES FOR CONTROLLED RELEASE OF ACTIVE INGREDIENTS

BACKGROUND OF THE INVENTION

The term "controlled release" refers generally to techniques for administering an agent wherein the agent is released in a certain manner affecting either the location or the timing of the release. Controlled release techniques have particular advantages in the context of administering therapeutic agents. For example, the release rate of a drug can be predicted and designed for an extended duration; this eliminates problems associated with patients neglecting to take required medication in specified dosages at specified times. Many drugs have short half-lives in the body before being removed. Trapping these drugs in polymeric matrices increases the time in which the drug maintains its activity. Further, the site specific localization of a drug achieved with a targeted delivery technique reduces or eliminates systemic side effects that certain medications cause when administered orally or intravenously.

There are several general types of controlled release systems. For example, drug release can be diffusion controlled, meaning that the diffusion of the agent trapped within a polymer matrix is the rate-determining factor for the overall release rate. Erosion based systems also exist in which a polymer degrades over time and releases a drug in an amount proportional to the gradual erosion. An osmotic pumping device uses osmotic pressure as the driving force for release. A fourth system is based on the swelling of a polymeric matrix, such as a hydrogel. Hydrogels are polymers that absorb and swell in an aqueous environment. The release of the agent is dependent on the volume increase of the gel upon swelling.

One mechanism which utilizes swelling for controlled release involves the movement of an elution solvent into a polymer matrix. The solvent must be thermodynamically compatible with the polymer. The solvent moves toward the core of the matrix at a constant velocity, which is a factor in determining the release rate of the solute drug (Ritger and Peppas, 1987). The penetration of the matrix creates stresses between polymer chains. In order to accommodate these stresses, the chains respond by moving and increasing their end-to-end distance. This response causes a lowering of the polymer's glass transition temperature ($T_g$), and mesh size (free volume between the chains) increases to swell the polymer. The increased mesh and increased mobility of the chains in the swollen region result in increased permeability of the polymer to the solvent (Korsmeyer and Peppas, 1984). In pH sensitive polymers, the pH of the environment influences the release rate of the solute by affecting the swelling behavior of the gel (Brannon-Peppas and Peppas, 1989).

One context in which the use of controlled release systems has been investigated involves the treatment of urinary tract infection associated with ureteral catheters or stents. The ureter functions as a pathway for urine leading from the kidney to the bladder. Obstruction of the temperatures the placement of a ureteral stent to open the pathway and assist in the passage of urine or the passage of the cause of the obstruction, such as kidney stones. The uretral stent functions by dilating the ureter to allow urine to flow and may also act as a guide for urine within the ureter, using the holes located along the length of the catheter.

Although stenting is an effective technique for aiding in the passage of both urine and stones, the presence of the device in the ureter can cause complications. According to Kunin, 40% of all-hospital-associated infections are related to the urinary tract (Kunin, 1987). Of these urinary tract infections, 80% are a consequence of catheterization (Fowler, 1989). After only one week of indwelling catheterization, the risk of infection is about 50%. Such catheterization is used in about 20% of patients in chronic care facilities such as nursing homes. More than 50% of these patients experience encrustation and blockage of their catheters, which inhibits the flow of urine. Inhibited flow can lead to a host of more serious problems for the patient if not corrected.

There are at least three possible mechanisms by which a catheterized ureteral area becomes infected. Bacteria can be introduced during the insertion of the stent, or the organisms can enter the urinary tract through the urethral meatus and subsequently migrate along the stent. The third possibility is that the bacteria utilize their ability to rise within a volume of fluid. The bacteria can actually migrate up the urinary tract via the urine (Franco et al., 1990). Once the bacteria have been introduced and colonize an area it takes only 24–48 hours for a relatively low concentration of bacteria ($10^2$–$10^4$ ml) to grow into a clinically significant population ($\geq 10^5$/ml) (Stamm, 1991).

Once established, the bacteria migrate along the catheter aided by the formation of biofilms (Nickel et al., 1992). Biofilms are aggregations of microorganisms surrounded by an extracellular matrix of exopolysaccharide (Swartz et al., 1991). The bacteria are sandwiched between this polysaccharide coat and the catheter. Therefore, the bacteria are isolated and separated from the surrounding ureteral environment. This isolation can lead to complications in executing an effective therapy against the bacteria due to their protection within the biofilm (McLean et al., 1991).

Certain species of bacteria such as the Gram-negative microbe *Proteus mirabilis* secrete the enzyme urease that degrades urea in the urine to form carbon dioxide and ammonia. The presence of ammonia increases the pH of the urine leading to the precipitation of magnesium ammonium phosphate salts and certain calcium phosphate salts. Struvite, hydroxyapatite, and carbonate apatite account for 10–20% of urinary encrustations (Olson et al., 1989). Although this fraction is small, the presence of these encrustations is considered a more significant risk to health than the presence of other stones because of their high growth rates.

Catheters dipped and-coated in antibiotic solutions have been produced to address the problem of infections developing with ureteral catheterization. See, for example, Izumi et al., EP 0 065 885; Whitbourne et al., EP 0 426 486; and Soloman, U.S. Pat. No. 4,999,210. Prophylactic use of antibiotics to control the bacteria that cause these encrustations, however, has proved unsatisfactory. Despite use of antibiotics, such as ciprofloxacin, given systemically, bacteria grow and multiply within the slime layer on urinary catheters. Continuous use or release (Reid et al., 1993; Soloman and Shevertz, 1987) of antibiotics in the absence of infection is of debatable merit because of drug side effects and the possibility of producing resistant strains.

Prevention of encrustation can be achieved by using a grease inhibitor to prevent the degradation of urea. The urease inhibitor competes with urea for active sites on the urease molecule. Various chemicals have been studied for their effect on the activity of urease and the crystallization of struvite (ammonium magnesium phosphate). Chondroitin sulfate and heparin sulfate have proven ineffective in preventing struvite encrustation. Sodium citrate shows potential; however, the mechanism of control does not involve the actual hahibition of urease but involves a possible complexation of the $Mg^{++}$ ions (McLean et al., 1990). Silver is used as a surface modification for preventing catheter bacteriuria (Liedberg et al., 1990).

Acetohydroxamic acid (AHA) is another option for prevention of urease-associated encrustation. It inhibits urease in a manner similar to boric acid (Breitenbach and Hausinger, 1988). Acetohydroxamic acid has been shown to be rapidly metabolized with a half-life of approximately five to ten hours (Takeuchi et al., 1980).

In selecting a stent or catheter, certain characteristics are desirable. The material should not prompt an immune response. The tube should also be flexible enough to avoid discomfort to the patient during catheterization but stiff enough to allow easy insertion. The polymer composing the stent should be sterilizable and should maintain its mechanical properties throughout the duration of implantation (Brazzini et al., 1987; Mardis, 1987). Common ureteral stent materials include: C-FLEX (styrene-ethylene/butylene block copolymer modified with polysiloxane); polyurethane; silicone; and SILITEK.

Hydrogels absorb water and swell in aqueous environments. Hydrogels are usually polymerized from a hydrophilic water-soluble monomer such as acrylic acid and crosslinked to yield a network polymer. When water is absorbed, the crosslinks prevent the polymer from dissolving, and the polymer swells (Tarcha, 1991).

Hydrogels have been used for many medical applications including contact lenses and surgical drainage tubes (Lee, 1988; Pearce et al., 1984). Hydrogels have also been used for coating urinary catheters or have actually been formed in the shape of a tube for use as a catheter (Ramsay et al., 1986). Upon swelling, the hydrogel's coefficient of friction is reduced, and the polymer becomes slippery. This property makes insertion and removal of the catheter less traumatic and recluces the inflammatory response of the urothelial tissue. Controlled release of active agents, such as antibiotics, from hydrogels is another application that is advancing rapidly (Soloman and Sheretz, 1987).

BRIEF SUMMARY OF THE INVENTION

The subject invention concerns a method for the controlled release of an agent from a pH sensitive polymer. The agent is released from the matrix of a polymer gel when the pH of the surrounding environment reaches a desired level. This method of controlled release can be used to ensure that the agent is delivered to a specific area and delivered only when the need for the agent arises. Methods such as these are also sometimes called stimulated, regulated, or triggered release.

A polymer gel comprising hydrophobic, weakly acidic comonomers will swell more in a basic environment than in a neutral or acidic environment and may be used to effect the controlled release of a biologically active agent. In a preferred embodiment, elastomeric polymers comprising butylmethylacrylate and methacrylic acid may be used according to the subject invention. Further, a hydrogel polymer comprising the comonomers methyl methacrylate and acrylic acid can be used according to the subject invention. The swelling behavior of this polymer was measured and determined to be pH sensitive due to the presence of the acrylic acid moieties. In this embodiment, the greatest swelling occurs at a pH value of 9.0.

Specifically, a copolymer hydrogel made of 90% methyl methacrylate and 10% acrylic acid was synthesized. The crosslinking agent diethyleneglycol dimethacrylate and the initiator 2,2'-azobisisobutyronitrile (AIBN) were used. Acrylic acid and methyl methacrylate were purified by distillation before use. The acrylic acid groups throughout the polymer chains ionize in a basic environment, and swelling subsequently occurs. A biologically active agent trapped within the polymer matrix is released into the environment upon swelling of the matrix.

In a specific embodiment of the subject invention, the exemplified hydrogel polymer is coated onto a surface. Upon swelling in an alkaline environment, this hydrogel releases a preloaded therapeutic agent for preventing or reducing the production and precipitation of magnesium ammonium phosphate hexahydrate (struvite). In a preferred embodiment, the agent of choice is acetohydroxamic acid (AHA), a known urease inhibitor. This drug competes with urea for the active sites on urease, an enzyme secreted by many bacteria, such as *Proteus mirabilis*, which infect the urinary tract. This competitive inhibition prevents the production of ammonia, which is the impetus for struvite precipitation.

The drug release profile of the exemplified hydrogel polymer used in the claimed controlled release method was observed and recorded. We discovered that acetohydroxamic acid experiences zero-order release from the polymer matrix with both diffusional and swelling control. The agent is released at the greatest rate and magnitude at pH 9.0.

The activity of acetohydroxamic acid in inhibiting urease was measured. It was determined that the inhibitor functioned to reduce the pH increase of urine at concentrations released by the hydrogel. Thus, the acetohydroxamic acid release system of the subject invention can be used in therapy for the prevention of urease-induced ureteral catheter encrustation.

To adjust the flexibility of the coating, various combinations of monomer can be used, or the active composition (pH sensitive polymer plus antibiotic) can be formed into microspheres and incorporated into an elastomeric matrix in the same way that a filler, such as $SiO_2$, is currently used in an elastomer such as silicone.

DETAILED DISCLOSURE OF THE INVENTION

One embodiment of the subject invention involves a coating for latex catheters which releases an antibiotic or other biologically active agent only when the environment becomes basic. For example, the agent may be released above a pH of about 8.5. The coated catheter can be used to reduce encrustation associated with struvite production, which is due to ammonia formation in bacteria-infected urine. The coated catheter with the on-demand release system further avoids problems associated with continuous slow release systems.

Release of an antibiotic when bacterial surface growth is present, but not at other times, advantageously controls bacterial growth without the excessive release of antibiotics. A specific embodiment of the subject invention concerns a pH responsive polymer or hydrogel which is useful for the pH stimulated release of an antibiotic into infected urine. Bacterial presence is detected by sensing a pH change induced by the urease-producing organism which causes the release of basic ammonia into the urine. High pH causes minerals in the urine to precipitate, forming encrustations. A pH-sensitive polymer such as a weak carboxylic acid can be used so that when the pH increases, ionization occurs and the polymer becomes swollen, causing antibiotic to be released which kills the urease-producing bacteria. Control of these bacteria helps regulate urine pH.

A second novel approach to the inhibition of stent encrustation is directed toward the control of the formation of the encrustation. Urease enzyme produced by the infecting bacteria is believed to be a primary factor resulting in the precipitation of magnesium in the urinary tract. Competitive inhibition of urease may be achieved through the use of acetohydroxamic acid (AHA), a stable synthetic compound derived from hydroxylamine and ethyl acetate. Its molecular structure resembles urea. Acetohydroxamic acid (AHA) has a molecular weight of 75.07 g/mole and a melting point range of 89–91° C. The pKa of AHA is 9.3. The mechanism of inhibition is the competitive binding of the amic acid group to the urease (Wu et al., 1985). As the acid binds to the enzyme, the number of available active sites for the binding of urea decreases, and less urea is degraded. The pH of the urine, therefore, does not become as alkaline. The effectiveness of this agent has been shown in other studies (Soriano et at, 1987; Griffith et al, 1988). The release of acetohydroxamic acid can be measured using UV/VIS spectrophotometry. The drug reacts with $FeCl_3$ to form a colored complex that absorbs light at 515 nm.

Despite being well absorbed from the gastrointestinal tract, AHA use is potentially limited by the development of Coomb's hemolytic anemia, GI complaints, bone marrow depression, and teratogenicity in patients. The local release of AHA by the methods of the subject invention can be used to increase concentrations of the unmetabolized drug administered to a patient while reducing the drug's potential side effects. AHA can be bound to catheter material by a hydrophobic/unionized polymer such as styrene/p-hydroxy styrene copolymer. These polymers swell in a pH greater than about 8.5, resulting in the controlled release of AHA only in the presence of increased urine pH (indicative of a urease-producing bacterial infection). Other useful polymers include substituted acrylates and also p-hydroxystyrene polymers and copolymers.

A polymer having a high glass transition temperature (105° C.) may be suitable to coat the body of the catheter; however, it is not possible to coat the expanding balloon at the tip of the catheter with this material. Simply coating the body of the catheter may be sufficient; however, the method more generally applicable to commercial use is a simple dip coating of the whole catheter. Therefore, the subject invention includes the use of not only glassy polymers but also elastomeric polymers capable of releasing an agent in a basic environment.

Two types of changes can be exploited in preparing polymers and materials to be used according to the subject invention. These changes adjust the release rate of the agent. First, the copolymer composition can be adjusted so that the agent being released is less soluble or mobile within the gel layer. Permeability (P) is equal to the mobility and concentration within a matrix and is usually expressed as the diffusion coefficient (D) times the solubility in that matrix (S), i.e., P=D·S. All elastomers have a higher free volume (greater than 2.5% ) than other materials that have glass transition temperatures below their own, such as polystyrene. Hence, it is likely that the mobility part of permeability would be greater in cases where elastomers are employed instead of glassy systems.

Hence, the solubility portion of the relationship must be adjusted to decrease the overall permeability. There are a number of elastomeric compositions that may be used according to the subject invention that have a sharply different solubility parameter than many of the commonly used therapeutic agents. For instance, fluoro elastomers are available by polymerizing fluoro-substituted alkylmethacrylates with methacrylic acid. In addition, simply using long hydrocarbon chains will have a very low solubility for water soluble agents such as hydroxamic acid. The copolymer composition also allows one to make shifts in the transition of pH-sensitive swelling to either a higher or lower pH value.

The other broad type of change that can be made to adjust agent release rate is to adjust the molecular weight of the diffusing therapeutic agent by selecting a different agent. There is a variety of broad spectrum antimicrobials which can be used to kill all bacteria present when released from the gel. These range from very low molecular size molecules such as silver ion (silver incorporated in a soluble form) to intermediate molecular weight species such as chlorohexidine, and, finally, to larger antimicrobials such as gentamicin. The larger the molecular size, the lower the diffusion rate will be through the matrix, given comparable solubility. Those skilled in the art can select and utilize many combinations of coatings and agents that can be adjusted to release at a basic pH.

The on-demand controlled release method of the subject invention is particularly advantageous because the antibiotic is only released at times when contaminating bacteria are present. Antibiotic is not continually released. There are at least three important advantages of this action: (1) tissue damage is restricted significantly compared to either continuous release or high level bolus instillation, (2) drug-resistant bacteria are not selected for growth since there are no much lower or ambient levels of antibiotic present, and (3) fewer side effects due to systemic absorption occur because total levels of antibiotic needed are lower.

Another advantage of this delivery method is that devices comprising the hydrogel polymer do not need to be antibiotic-loaded at the time of sale; instead, they may be loaded by solvent or pH-induced swelling before use by the personnel inserting the device.

It should also be noted that this system does not prevent applying an additional hydrogel layer as the outermost layer on a catheter. The innermost layer of the Foley catheter can be a standard elastomer for mechanical properties. A second layer can be the pH sensitive releasing layer. The final layer can be a hydrophilic coating such as is currently used on many catheters. Additionally, microspheres made of the polymer compositions of the subject invention can be incorporated into one of the layers. Such microspheres need to swell only a very small amount to begin release and once again give a pH release profile from an otherwise mechanically or lubricity functioning polymer layer.

Although the subject invention is specifically exemplified with a single embodiment, it would be apparent to one skilled in the art that the controlled release method of the subject invention is useful for a number of applications. Specifically, the controlled release polymers of the subject invention can be used for other types of indwelling devices, such as heart valves, pacemakers, artificial joints, or devices that are inserted into the body cavity such as gastrointestinal tubes, intrauterine devices, or diaphragms. The polymer matrix utilized within these devices can be triggered to release biologically active agents when the pH of the environment turns either acidic or basic. This change in pH may be due to changes occurring naturally in the environment or changes induced by an operator. For example, at a desired time, the operator may release a basic reagent into the environment of the polymer to effect the desired release of the agent entrapped in the polymer matrix. Additionally, the claimed method is applicable to a variety of non-health care uses, including industrial settings in which it is desirable to have an agent released at a certain pH. Such uses can include all types of surfaces including, but not limited to, pipes, food production equipment, or chemical vats. The controlled release polymer can be incorporated into cat litter or other pet products which will release an antibiotic or deodorant upon a change of pH associated with urine, as well as fabrics and diaper materials.

Polymer synthesis. A modified suspension polymerization method (Batich et al., 1993) can be utilized. Monomers are freed from the inhibitor by washing with aqueous NaOH or by distillation. Solubility of a weak acid monomer (p-hydroxystyrene or methacrylic acid) can be reduced by working in acid aqueous solutions with NaCl added as needed to salt out the monomer. In a high speed stirrer (c. 300 rpm) equipped 500 ml flask under nitrogen, 200 ml of pH 3 buffer (with NaCl as needed) are introduced and stirring is commenced. A suspension stabilizer such as polyvinyl alcohol can be added as needed (about 0.5 g). A well mixed solution of monomers (20 ml) containing 0.2 g AIBN is added and stirring continued while heating to 70° C. for four hours, then 80° C. for three hours. The reaction products can be filtered and washed with pH 7.0 buffered methanol and then dried. Modifications in the initiator, stabilizer, and reaction conditions used can be made by those skilled in the art utilizing the subject disclosure. Polymer can be purified by dissolving in an organic solvent such as tetrahydrofuron (THF) or acetone and precipitating in water. For microsphere synthesis, a similar method is used except divinylbenzene cross-linking agent is added to the monomer mix to make a 1% solution of organic components (i.e., 0.2 g in the 20 g).

To simplify expected polymer compositions, styrenics can be reacted with themselves, and acrylates with themselves, although styrenics can also be reacted with acrylates. The monomer p-octylstyrene can be used with p-hydroxystyrene and styrene. A separate series of reactions can be done using methacrylic acid and n-alkyl acrylates. Poly-n-octylacrylate has a brittle point of −60° C. (Saunders, 1988) and should be elastomeric and hydrophobic enough to provide reasonable release profiles.

Linear polymers can be prepared by solution methods in organic solvents. The suspension products provide a geometry easy to use for swelling studies. Butyl and hexyl acrylates, as well as decylmethacrylate, form soft polymers at room temperatures and are usable hydrophobic monomers. These monomers are commercially available from several sources (e.g., Aldrich, or Dajac Laboratories). Extreme hydrophobicity can be achieved by using perfluoroacrylates, such as tetrahydroperfluorodecyl methacrylate.

Measurement of swelling. For small drug molecules, only a few percent swelling of the matrix is necessary to allow release. For release of gentamicin or other larger drug molecules, greater swelling is needed. Swelling can be controlled by cross-link density.

For suspension polymerized glassy polymers, equilibrium is achieved within about two days (usually within one day), although swelling commences much more quickly. Elastomers will swell faster.

About 0.4 g of microsphere beads are immersed in 100 ml buffer at 25° C. for two days with the buffer being replaced several times to reach a constant pH on the first day. The water content can be determined by the centrifugation method described by Pepper (Pepper et al., 1952) where swollen beads are transferred to a filter tube and centrifuged to remove most of the water. The tube is then weighed and dried in a vacuum oven at 70° C. to a constant weight. The change in weight represents absorbed water and is reproducible to less than 2% when water contents are 75%.

Citrate buffers can be used and adjusted to an ionic strength of 0.3M with NaCl. An Orion pH meter is used to monitor pH values.

Drug Loading

Comonomers having greater hydrophobicity tend to swell to a larger extent in ethanol than in water. Hence, the copolymers can be loaded with the agent by swelling the microspheres or film coatings in ethanol containing a high concentration of an alcohol soluble drug. Gentamicin, chlorhexidine, and hippuric acid are all highly soluble in alcohols. Ethanolic solutions containing from about 15% to about 30% drug are heated to 50° C. and the polymer placed in them for about 1 hour. Upon removal, the polymer is placed in a vacuum oven at 50° C. for several hours (until constant weight). The polymer is then be washed with neutral water to remove surface deposits of drug. The amount of drug incorporated can be determined by extraction with dilute aqueous sodium hydroxide (more basic than pH=10.0) and measurement of the released drug by spectrophotometry.

Very low concentrations of gentamicin are normally used in plasma (less than 2 mcg/ml) because of systemic nephrotoxicity. For slow release, levels will be highest at the surface of the catheter where the bacteria grow. Gentamicin has been shown to be highly effective against *Proteus* sp. and other urease-producing organisms. Because the volume of liquid adjacent to a catheter is small and the removal rate for this layer is low (there is no urine or blood flow at this interface), release rates of about 0.1 mcg/min for a one-inch segment of catheter can be used. Hence, at least about 1.4 mg of gentamicin can be loaded in each one-inch segment of catheter.

Measurement of Drug Release

One-inch segments of coated Foley catheters may be placed in 100 ml of 37° C. buffer at pH 7.4 and also 9.0. A 5 ml aliquot of the buffer solution is removed at 4 hours, 8 hours, and 24 hours for analysis by UV-spectrophotometry. The 5 ml will be replaced with fresh buffer each time. The exact drug being released is less important than demonstrating the mechanism of stimulated release. Therefore, other easily observed agents such as fluorescein or tetracycline which absorb light in the visible range and have larger extinction coefficients than gentamicin may be used to test drug release. If difficulties arise with simple spectrophotometric detection at low levels, concentration by evaporation, or switching to an HPLC method can be used.

Following are examples which illustrate procedures, including the best mode, for practicing the invention. These examples should not be construed as limiting. All percentages are by weight and all solvent mixture proportions are by volume unless otherwise noted.

Example 1—Methyl Methacrylate/Acrylic Acid Hydrogel Synthesis

Various polymer compositions were synthesized. Table 1 shows the parameters that were varied. The monomers used were acrylic acid (AA) and methyl methacrylate (MMA). If the percent of monomer was less than 100, then the cosolvent was distilled water. Crosslinking agents used were diallylamine (DA), which is pH sensitive; tetraethyleneglycol dimethacrylate (TEGMA); diethyleneglycol dimethacrylate (DEGMA); and ethyleneglycol dimethacrylate (EGMA). The initiators were ammonium persulfate for the aqueous polymerizations and 2,2'-azobisisobutyronitrile (AIBN) for the organic polymerizations. It was determined by visual inspection of the swelling properties in water that, of the different polymer compositions listed here, the MMA-JAA (90/9) polymer displayed the least solvent absorption.

TABLE 1

Experimental parameters for polymer synthesis

| monomer (%) | % monomer | crosslinker (%) | initiator (%) | reaction time (hr) |
| --- | --- | --- | --- | --- |
| AA (100) | 60 | DA (2) | AP (0.5) | 4 |
| AA (100) | 40 | DA (2) | AP (0.5) | 4 |
| AA (100) | 20 | DA (2) | AP (0.5) | 4 |
| AA (100) | 40 | DA (5) | AP (0.5) | 4 |
| AA (100) | 60 | DA (10) | AP (0.5) | 4 |
| AA (100) | 60 | DA (15) | AP (0.5) | 4 |
| AA (100) | 60 | DA (20) | AP (0.5) | 4 |
| AA (100) | 60 | TEGMA (5) | AP (0.5) | 4 |
| AA (100) | 60 | DEGMA (5) | AP (0.5) | 4 |
| AA (100) | 60 | EGMA (5) | AP (0.5) | 4 |
| MMA/AA (90/10) | 100 | DEGMA (1) | AIBN (0.5) | 24 |
| MMA/AA (85/15) | 100 | DEGMA (1) | AIBN (0.5) | 24 |
| MMA/AA (80/20) | 100 | DEGMA (1) | AIBN (0.5) | 24 |
| MMA/AA (70/30) | 100 | DEGMA (1) | AIBN (0.5) | 24 |
| MMA/AA (60/40) | 100 | DEGMA (1) | AIBN (0.5) | 24 |
| MMA/AA (90/9) | 100 | DEGMA (1) | AIBN (0.5) | 24 |

See text for definitions of abbreviations.

Two equally sized glass plates were clamped together separated by a silicone tube. The tubing was manipulated into the shape of a "U" with the ends extending beyond the edge of the glass, forming a well or mold for placing the monomer solution. The inner surfaces of the mold were coated with Sigmacote, a silicone solution used to prevent the glass plates from sticking to the polymer gels. Acrylic acid (Sigma, St. Louis, Mo.) was distilled at 56° C. and 20 mmHg. Methyl methacrylate (Sigma) was distilled at 58° C. and 160 mmHg. Table 2 lists the reactants and amounts that were used for the polymerization.

TABLE 2

Reactants for hydrogel synthesis

| Reactant | Amount (g) |
| --- | --- |
| acrylic acid | 9 |
| methyl methacrylate | 0.9 |
| DEGMA | 0.1 |
| AIBN | 0 |

The two monomers were mixed, and the initiator and crosslinking agent were mixed in separate containers. These two mixtures were then mixed together with a stir bar for approximately 10 minutes. For polymerizations in which water was a cosolvent, degassing with argon was done to remove $O_2$ radical scavengers. The monomer solution was then placed into the glass molds by loading it into a syringe and then dispensing the solution into the mold. The molds were placed into a 60° C. oven for 24 hours. After polymerization, the gels were soaked in a 90 v/v % ethanol solution at 37° C. for approximately 48 hours, with changing of the solvent after 24 hours. The ratio of extraction medium to polymer was approximately ten to one. This soaking was done to remove any residual monomer or oligomers present in the polymer. At 24 hours, the characteristic odor of methyl methacrylate could be detected in the ethanol solution. The odor was absent at 48 hours. The gels were cut into square shaped pieces and dried under vacuum at 60° C. Polymerization of the hydrogel with the AHA dissolved in the monomer was attempted, but the reaction did not occur, probably due to blocking of the radicals necessary for this type of polymerization.

Figure 1:
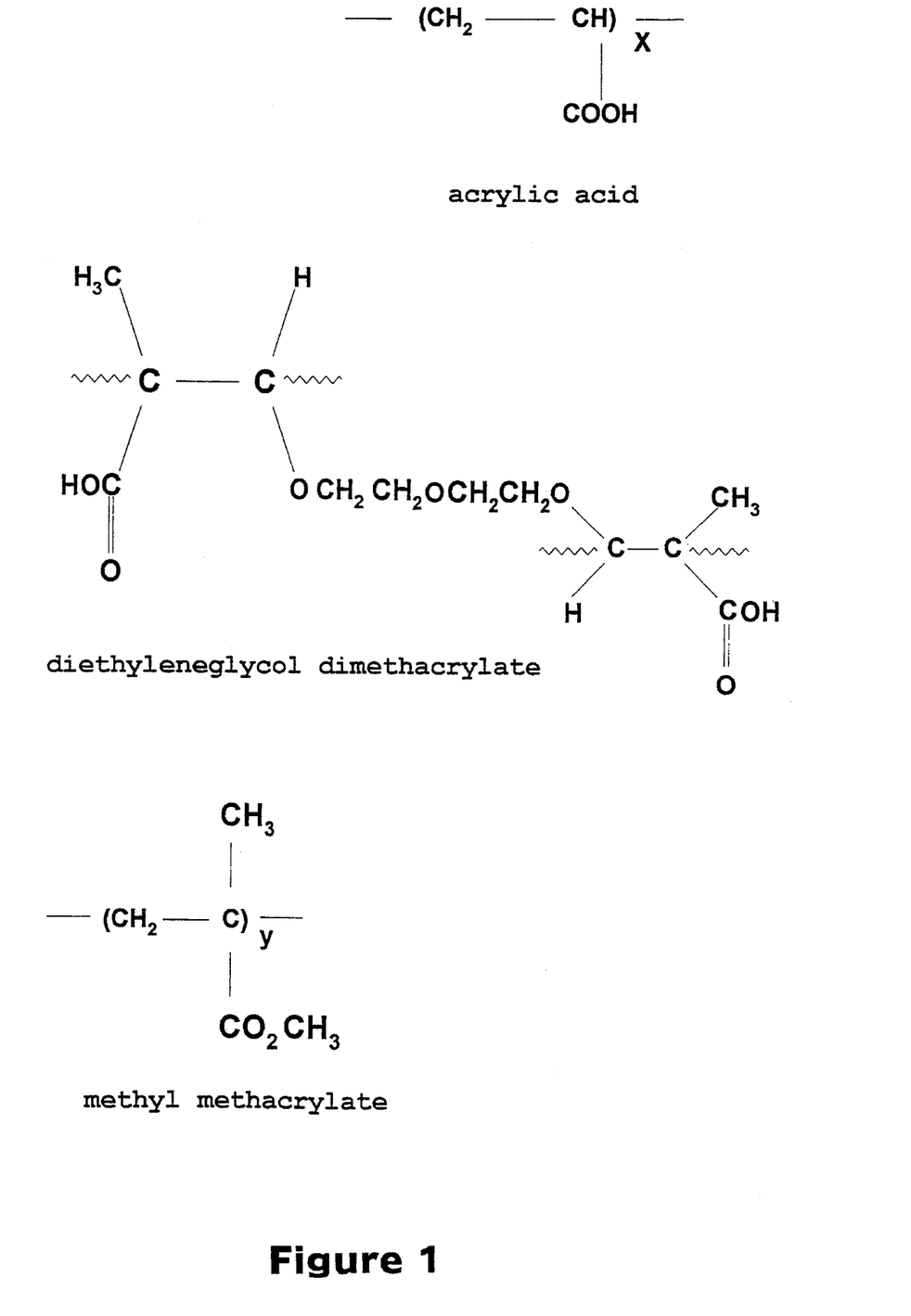
FIG. 1 is the structure of the methyl methacrylate/acrylic acid copolymer hydrogel exemplified by the subject invention.

FIG. 1 shows the structure of the copolymer synthesized that was subsequently used for drug release assays. The crosslinker is shown in the center. The lines extending from either end of the dimethacrylate molecule represent the polymer chains composed of methyl methacrylate and acrylic acid. The exact values of "x" and "y" in the structure are unknown; however, an estimate can be calculated using the reactivity ratios of the monomers. The reactivity ratio for methyl methacrylate ($r_1$) is 2.150 for a copolymerization with methyl acrylate, the methyl ester of acrylic acid. Methyl acrylate has a reactivity ratio ($r_2$) of 0.400 (Greenley, 1989). Therefore, both monomers preferentially add methyl methacrylate. The mole fraction of methyl methacrylate in the copolymer ($F_1$) can be calculated from equation one (Odian, 1981).

$$F_1 = \frac{r_1 f_1^2 + f_1 f_2}{r_1 f_1^2 + 2 f_1 f_2 + r_2 f_2^2} \qquad (1)$$

The mole fraction of each monomer before polymerization is given by $f_1$ for methyl methacrylate and $f_2$ for the comonomer. The calculated value of $F_1$ is 0.95, which means that the bulk of the polymer will be composed of methyl methacrylate, yielding a predominantly hydrophobic polymer.

Example 2—Hydrogel Swelling Study

The swelling behavior of the synthesized hydrogel was observed at pH values of 4.0, 5.0, 7.4, and 9.0. All buffers were purchased from Fisher Scientific (Pittsburgh, Pa.). The pH 7.4 buffer contained 0.05M potassium phosphate monobasic and sodium hydroxide, and the pH 9.0 buffer contained 0.1M boric acid, potassium chloride, and sodium hydroxide. The pH 4.0 buffer contained a mold inhibitor that participated in a side reaction with the AHA detection solution. A citric acid buffer composed of citric acid and trisodium citrate adjusted to pH 4.0 was substituted. The buffer at pH 7.4 also reacted with the detection solution but not to the extent that the buffer at pH 4.0 did. The precipitate was filtered with a 2.0 μm syringe filter. Six dried hydrogel pieces were separated out for each pH being tested. Each individual piece was weighed and placed into a separate labeled test tube. Into each test tube 4 ml of buffer solution were pipetted. The test tubes containing both the polymer samples and the buffer were placed into a 37° C. water bath. Samples were removed from the test tubes at 24, 48, 72, 96, 120, 144, and 168 hours. The samples were blotted with a tissue in order to remove any excess buffer on the surface. After blotting, the samples were weighed and placed into the buffer again for further swelling until an equilibrium weight was reached. The swelling ratios of the gels were calculated for each time interval using equation one.

During the swelling study, the dimensional change that occurred in the hydrogel was unnoticeable. This small dimensional change is in contrast to the high swelling exhibited by the pure acrylic acid hydrogels synthesized by Park (Park, 1988). The differences in swelling can be attributed to the high concentration of hydrophobic methyl methacrylate in the polymer. The methyl methacrylate regions of the polymer form a barrier to aqueous solutions and hinder movement of the solvent front into the matrix. Therefore, the equilibrium volume of solvent that permeates the matrix is decreased.

Figure 2:
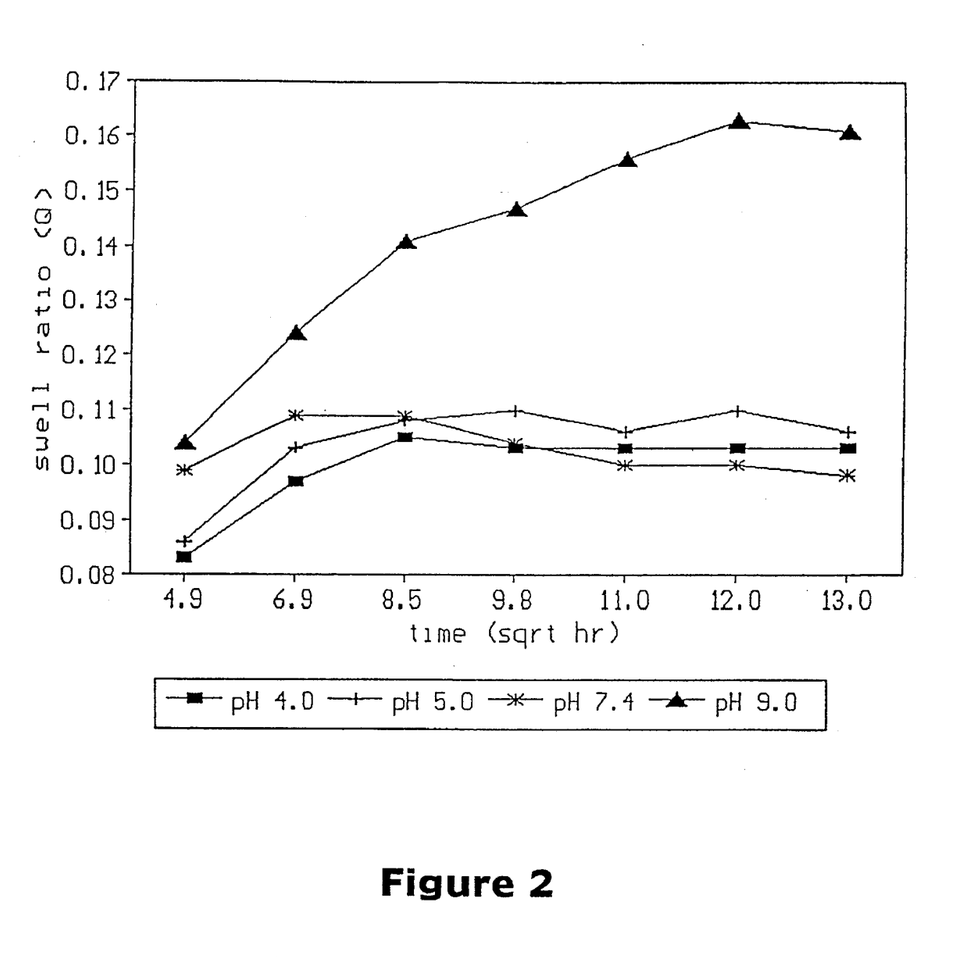
FIG. 2 shows the swelling behavior of the methyl methacrylate/acrylic acid copolymer hydrogel at various pH values.

FIG. 2 shows the swelling behavior of the MMA/AA hydrogel at four different pH values. As the pH of the swelling medium increases, there is a small increase in the swell ratio until the pH reaches 9.0. At this value, the polymer exhibits a marked increase in the swell ratio due to increased ionization of the acrylic acid. This increase at pH 9.0 is the desired effect for AHA release as the urease activity increases the pH to approximately 9.0 if allowed to proceed without therapy. The MMA/AA copolymer with an AA content of 9% exhibits behavior that disagrees with the observation of Bronstedt that, with 10% AA content, little pH sensitivity is seen in the polymer (Bronstedt and Kopecek, 1991). The samples in the pH 4.0, 5.0, and 7.4 buffers reached an equilibrium solvent content at approximately 48 hours while the samples in the pH 9.0 buffer did not reach equilibrium until approximately 144 hours. The maximum swell ratio reached at pH 9.0 was 0.16 compared to a minimum swell ratio at pH 4.0 of approximately 1.7 in a swelling study of poly(hydroxyethylmethacrylate) (HEMA) (Brannon-Peppas and Peppas, 1990).

One possible mechanism for the relatively high swelling observed at pH 9.0 is the hydrolysis of the MMA pendent groups to carboxylate groups which can then ionize and further increase the swelling (DeMoor et al., 1991). If degradation of the methyl methacrylate to acrylic acid occurred, it would be accompanied by a mass loss of the polymer. DeMoor found, however, that the swelling was slower at higher pH values but that the final equilibrium swell ratio was higher. The MMA/AA data do not agree with DeMoor's findings as the polymer swells faster and greater at pH 9.0. Eckstein et al. observed large volume changes between pH values of 6.0 and 7.0 in the HEMA hydrogel they studied for prevention of encrustation (Eckstein et al., 1983). This pH range is too acidic for the desired application of urease inhibitor release. If large swelling occurs before a significantly alkaline environment is produced, the AHA will diffuse out rapidly and be diluted and wash,ed away by the flow of urine through the ureter (60 ml/hr), leaving nothing to inhibit the activity of the urease. The swelling properties of the hydrogel of the subject invention were not measured after loading the polymer with the AHA, but it is suggested that the presence of a drug in the polymer increases the swelling. (Robert et al., 1987). The release of the drug was therefore studied as a function of pH. The release will depend on the pH related solubility of the drug as well.

Example 3—Hydrogel Drug Release Study

Six pieces of the MMA/AA (90/9) polymer were weighed in the dry state. Each piece was placed into 4 ml of a separate solvent. The solvents used were pH buffers with pH values of 4.0, 7.4, and 9.0, 90 v/v % ethanol, methanol, and 90 v/v % acetone at 37° C. This experiment was conducted to determine which solvent resulted in the most swelling of the gel for drug loading purposes, since the AHA is very soluble in all the chosen solutions. The results indicated that the 90% acetone solution elicited the largest swelling ratio. A 16 w/w% solution of acetohydroxamic acid in 90% acetone was prepared. This concentration was near the saturation point as more acetohydroxamic acid could not be dissolved in the solvent.

The drug release profile of the synthesized hydrogel was characterized at pH values of 4.0, 7.4, and 9.0. Hydrogel pieces were weighed in the dry state. Six pieces weighing approximately the same were separated out for each respective pH buffer value. Each gel piece was individually placed into a test tube containing 3 ml of the 16% AHA acetone solution. The test tubes were capped and wrapped in parafilm to prevent evaporation of the solvent. The test tubes were placed into a 37° C. water bath for 48 hours. The hydrogel pieces were then removed from the AHA solution and placed in a vacuum oven at 60° C. for solvent evaporation and then at room temperature for a total drying time of 72 hours. The drug-loaded gels were then reweighed, and the total AHA content was calculated.

For each drug-loaded hydrogel piece, a series of eight test tubes containing 4 ml of buffer solution was prepared. Each gel piece was placed into the first test tube labeled "1 hr" and remained there for 1 full hour at 37° C. At 1 hour, each piece was transferred from the first test tube to the second test tube labeled "2 hr." This procedure was repeated at 6 and 24 hours. Samples were dried, and the release was initiated again and measured at 24, 51, 72, and 105 hours. All solutions were then mixed with a Vortex mixer.

Standard solutions of AHA were prepared at concentrations of 750, 375, 187.5, 75, and 7.5 µg/ml by adding 0.075 g of AHA to a 100 ml volumetric flask and filling to volume with buffer. Serial dilutions of these concentrations were then performed. These standard solutions were prepared at pH values of 4.0, 7.4, and 9.0. A 0.1M solution of $FeCl_3$ was prepared by adding 13.516 g of $FeCl_3$ to a 500 ml volumetric flask and filling to volume with distilled water.

Three milliliters of the $FeCl_3$ were pipetted into a series of test tubes corresponding to test tubes in which the drug release studies were conducted. Into these test tubes 2 ml of the extraction buffer containing the released AHA were pipetted. The reactants were mixed, and a stable color was allowed to form. This procedure was also done for the standard concentration solutions.

Absorbances for each of the solutions were measured at 515 nm on a Perkin-Elmer Lambda 3B UV/VIS Spectrophotometer. A calibration curve was calculated from the standard concentration solutions. The concentrations of the AHA were calculated from the absorbantes and ratioed to the initial surface area of the gel matrix.

Maximum loading of the AHA was desired for the prolonged release required for effective control of the urease. This reason prompted the use of the 16% AHA solution in contrast, to other studies where lower percent loading solutions were used (Kou et al., 1988). The polymer seems to swell the most in the acetone solution. According to the *Polymer Handbook,* the ethanol solution is a solvent for both the MMA and AA, while acetone is not listed as such (Fuchs, 1989). The small increase in swelling of the gel in acetone might be attributed to the absence of hydroxyl groups and presence of methyl groups, leading to decreased miscibility of the solvent with water and increased miscibility with the polymer. Because the acetone solution caused maximum swelling of the polymer, the AHA was dissolved in this in order to maximize the loading capacity of the matrix. The drug loading of the polymer was approximately 13 w/w %.

Within the first 24 hours an initial burst of AHA was observed as recorded for other systems in other studies (Kim and Lee, 1992a). The gels released between 20% and 30% of their drug content. This initially high rate of release is probably due to a high surface concentration of the drug. According to Ritger and Peppas, zero-order release kinetics can be attained by any matrix geometry including the thin slab geometry used in this study (Ritger and Peppas, 1987). Therefore, the drug release was continued beyond 24 hours but, before continuing, the gels were removed from the extraction media and redried to eliminate the burst effect and prolong the release by reducing the surface concentration of AHA and creating a drug concentration gradient from the surface to the center of the matrix (Korsmeyer and Peppas, 1984; Mueller, 1987).

Figure 3:
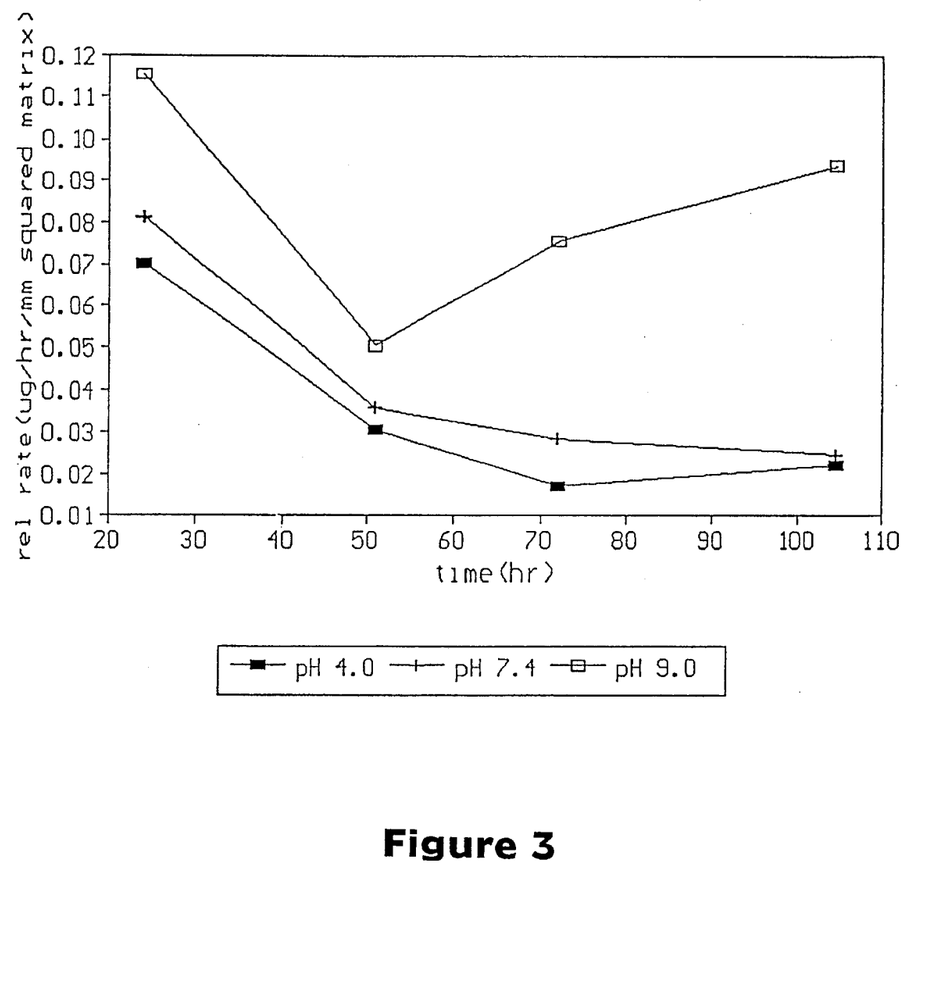
FIG. 3 shows the release rate of acetohydroxamic acid from the methyl methacrylate/acrylic acid matrix as a function of pH.

FIG. 3 shows the release rate of the AHA from the MMA/AA matrix. For the samples in both the pH 4.0 and 7.4 buffers, the rate decreases over the 24 hr to 51 hr period and then levels off while the samples in the pH 9.0 buffer exhibit a drop in release rate and then an increase. The decrease observed in all three can be explained by the burst effect.

Figure 4:
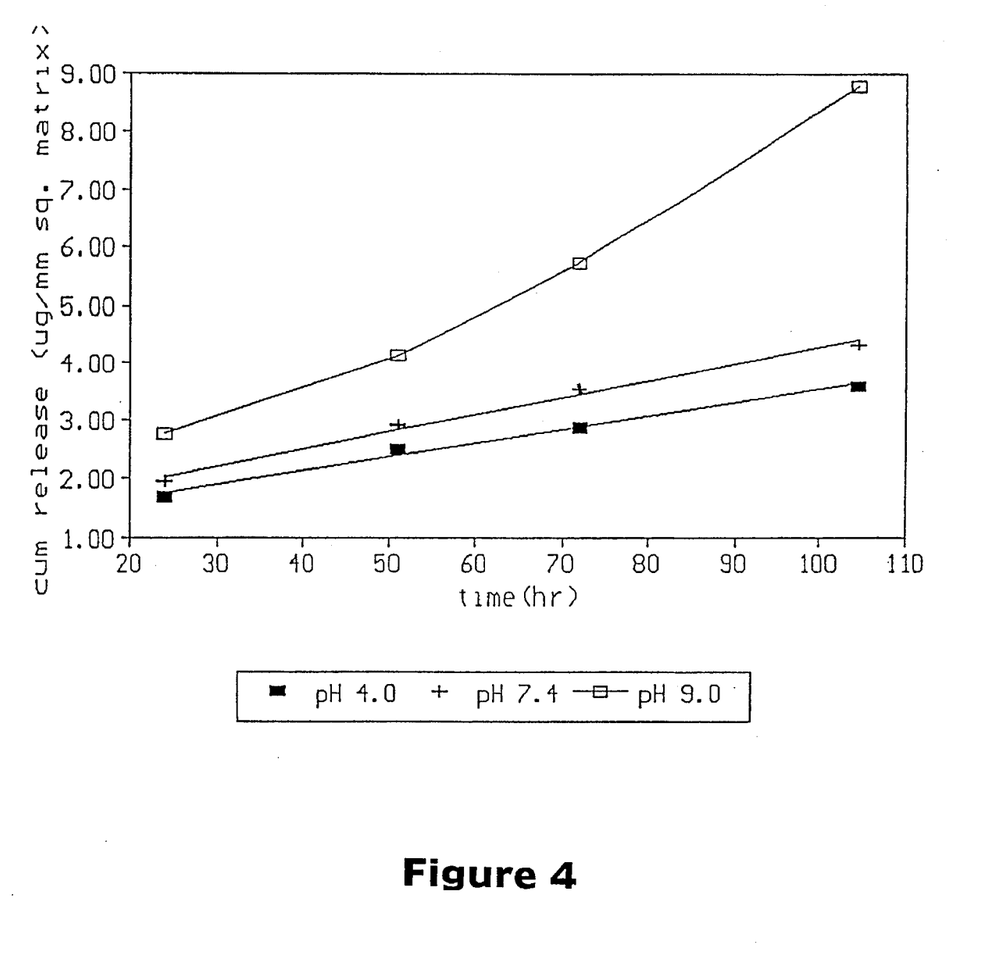
FIG. 4 shows the cumulative release of acetohydroxamic acid from the methyl methacrylate/acrylic acid hydrogel.

FIG. 4 shows the cumulative release of the AHA from the matrix. The curves for pH 4.0 and 7.4 lie along the datas calculated linear regression line, suggesting a release directly proportional to time. There is a slight increase in the slope of the curve for the samples in pH 9.0 buffer after 50 hours due to the increased swelling, but the curve is linear from this time until the conclusion of the experiment. The curves clearly indicate an increase in drug release at a PH of 9.0, a result of the increase in free volume in the matrix due to greater chain mobility and subsequent increased swelling resulting in an increased diffusivity of the solute. Only a slight increase in release can be observed in going from pH 4.0 to pH 7.4. The values shown in the graph are ratioed to the surface area of the dry matrix for comparison between samples. Therefore, the actual amount of AHA released by 105 hours ranges from 469 µg at pH 4.0 to 1224 µg at pH 9.0. The amount of AHA released at each interval ranges from 46 µg at pH 4.0 to 424 µg at pH 9.0. The concentration of the drug in the extraction medium at each interval ranges from 12 µg/ml at pH 4.0 to 106 µg/ml at pH 9.0. Therapeutic benefit can be achieved with a concentration of AHA as small as 7.5 µg/ml; therefore, enough AHA is being released from the hydrogel to effectively inhibit the urease. The graph also shows that release of the drug continues to occur even after equilibrium swelling has been reached. Kim and Lee found that solute release ceased as the swelling front reaches the center of the matrix, suggesting a swelling-controlled release (Kim and Lee, 1992b).

Figure 5:
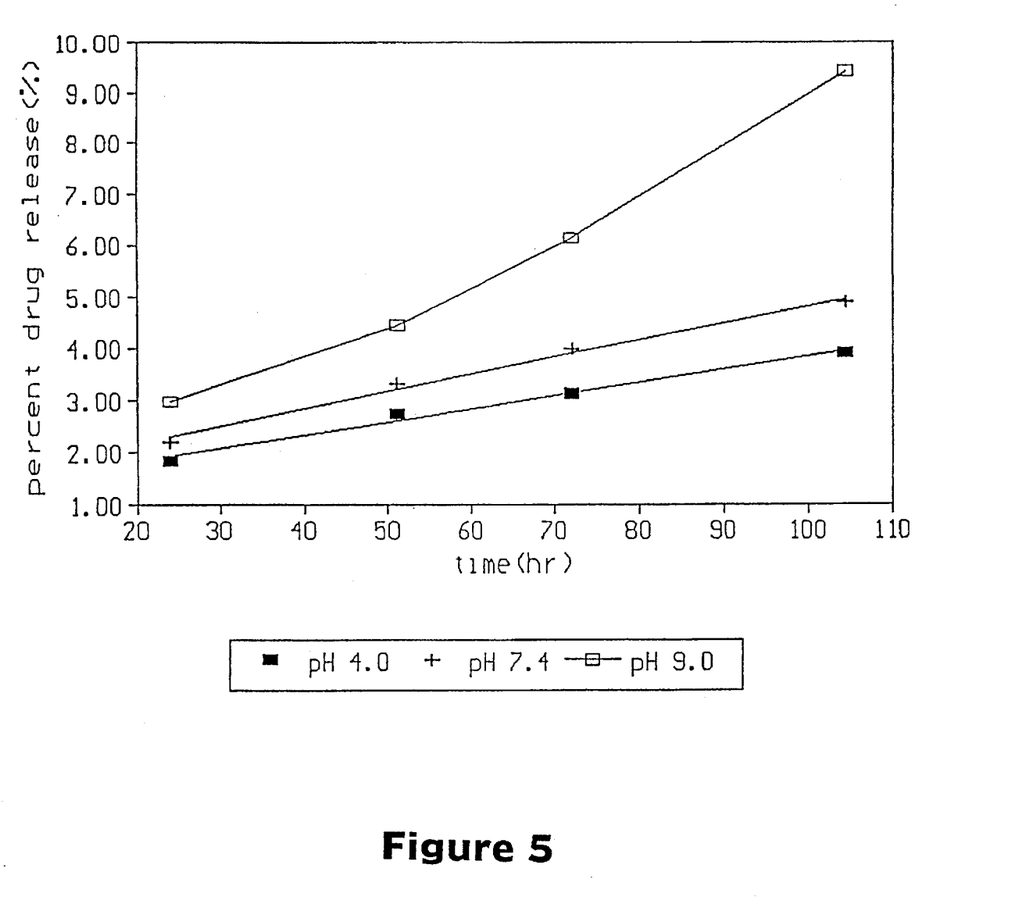
FIG. 5 shows the percent release of acetohydroxamic acid from the methyl methacrylate/acrylic acid hydrogel as a function of pH.

FIG. 5 shows the percent release of the AHA from the MMA/AA hydrogel. The general trend is observed again that as the pH of the extraction medium increases, the amount of drug released increases. At 105 hours, the percent of AHA released at pH 9.0 is almost 10%. Adding the initial release of approximately 20% to this value yields a total release of approximately 30%. This means that most of the drug remains in the polymer for further release. The 30% drug release at 105 hours at pH 9.0 is much less than the approximately 60% drug release exhibited by the HEMA/MA hydrogel used by Kou et al. (Kou et al., 1988). The relatively small amount of drug released must be a function of the composition of the polymer. The hydrophobic nature of the MMA in the matrix limits the swelling and therefore the release of the drug as compared to the hydrophilic nature of the HEMA polymer, which is more permeable to the extraction medium and swells more, allowing a greater diffusion of the solute. For the MMA/AA hydrogel, as the drug depletion zone moves toward the center of the matrix, the mobile hydrophobic chains can collapse and form a barrier to further drug release and extend the overall release duration (Mueller, 1987).

To reduce the release of AHA at acidic pH values, it would be apparent to one skilled in the art that the acrylic acid content of the polymer could be further reduced, making the polymer even more hydrophobic. A stronger barrier to aqueous environments would therefore result. The crosslink density of the polymer could also be increased. Chien has shown that, as the crosslink density increases, the diffusivity of solute decreases (Chien, 1992). One final option might be to substitute acrylic acid with a comonomer that is less readily ionized. Swelling would then be reduced.

Example 4—Bacteria/Urease Study

Artificial urine was synthesized with the composition shown in Table 3. After mixing, the urine was filter-sterilized into a sterile container using a 0.2 µm pore size filtration system. A solution of this artificial urine containing 750 µg/ml of AHA was prepared by dissolving 0.0757 g of the AHA in 100 ml of the urine. This solution was then diluted in series to yield artificial urine with AHA concentrations of 375, 187.5, 75, and 7.5 µg/ml.

TABLE 3

Composition of artificial urine

| Component | concentration g/liter |
|---|---|
| $CaCl_2.2H_2O$ | 0.65 |
| $MgCl_2.6H_2O$ | 0.651 |
| NaCl | 4.6 |
| $Na_2SO_4$ | 2.3 |
| $Na_3citrate.H_2O$ | 0.65 |
| $Na_2oxalate$ | 0.02 |
| $KH_2PO_4$ | 2.8 |
| KCl | 1.6 |
| $NH_4Cl$ | 1.0 |
| Urea | 25.0 |
| Creatinine | 1.1 |

Griffith et al., 1976

Fifty milliliters of these solutions were sterilized by filtering them through a syringe filter with 0.2 μm pore size into a sterile container.

Proteus mirabilis were harvested from the Surgery/Urology clinic at the University of Florida, Gainesville, Fla.. These bacteria were cultured on a heart infusion agar (Difco Laboratories) for 48 hours at 37° C. Bacteria were aseptically harvested and suspended in a solution of artificial urine not containing any of the urease inhibitor. Dilutions of this suspension were made to 10,000, and a count of the bacteria was made on a microscopic counting grid. The initial concentration of bacteria was back-calculated by using the Petroff-Hauser formula shown in equation $$[\text{bacteria}] = \frac{(\text{total count}) (\text{dil factor}) (2 * 10^7)}{\text{number of squares counted}} \quad (2)$$

For the urine solutions containing the urease inhibitor and two control solutions (one containing bacteria and the other without), a series of six test tubes was set up. Into these test tubes, 5 ml of each separate urine solution was pipetted. A 0.5 ml volume of nutrient broth was added to each of the test tubes to allow growth of the bacteria. Bacteria were then pipetted as aseptically as possible into each of the test tubes except the control samples, which contained no bacteria. The final concentration of bacteria in solution was approximately $10^{11}$ bacteria/ml. The test tubes were then mixed to obtain a homogenous mixture of bacteria and nutrient broth in the urine and placed in a 37° C. oven. The pH of each of the samples was measured initially and then at 2 hour intervals up to 12 hours. A final pH measurement was taken at 24 hours.

Figure 6:
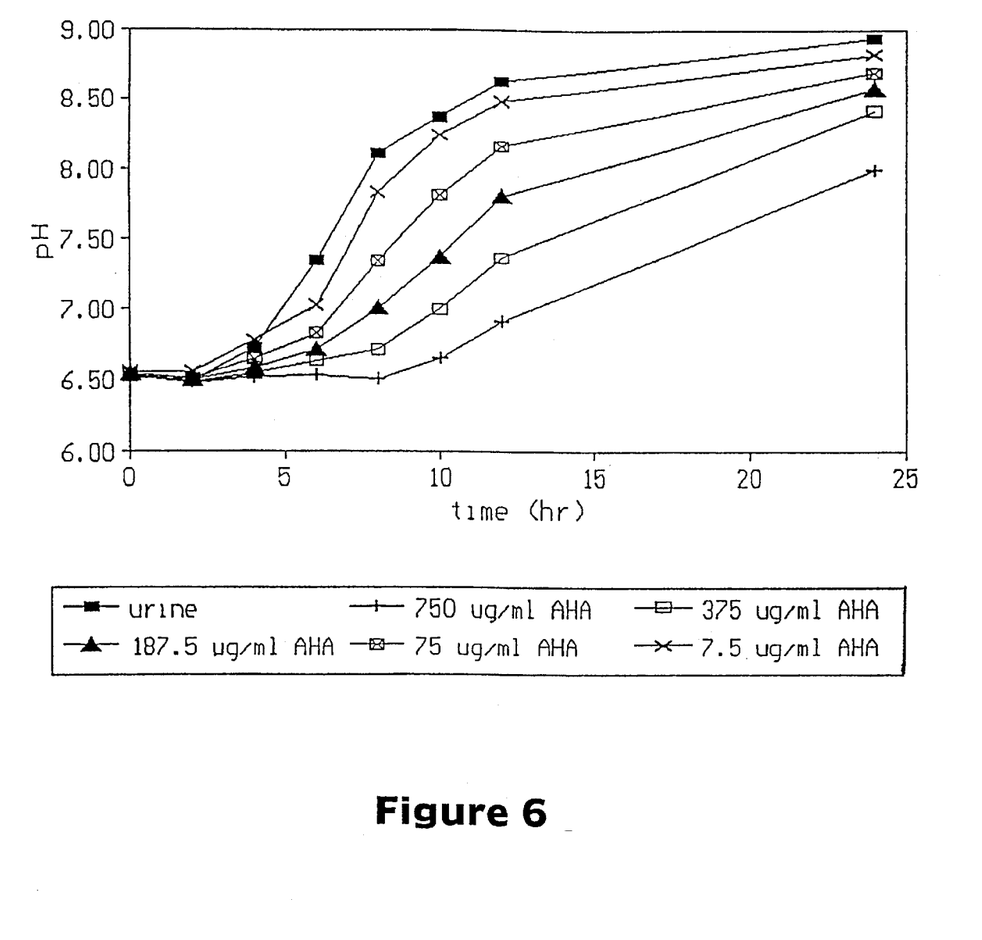
FIG. 6 shows the effect of acetohydroxamic acid on the activity of urease.

Artificial urine with concentrations of AHA corresponding to the concentrations of AHA used for the drug release study was prepared so that a correlation could be made between the amount released and the effect of this concentration on the activity of the urease. FIG. 6 shows the inhibitory effect of the AHA on the enzyme. Control samples with no bacteria present exhibited pH values ranging from 6.49 to 6.71 over the 24-hour period. As the concentration of AHA increases, the artificial urine resists pH increase for a longer time and experiences a smaller overall pH increase because there is more competition for the active sites on the urease molecule. More enzyme sites are blocked with the AHA and cannot react with the urea to form $NH_3$. With AHA concentrations released ranging from 12 μg/ml to 106 μg/ml, enough drug is being released to inhibit the urease. A high concentration of bacteria ($10^{11}$/ml) was used to test the effectiveness of the drug. In practice, bacteria concentrations of $10^5$/ml or more are considered significant. With this lower, more clinically relevant concentration of bacteria, the effect of the AHA should be more pronounced. The combination of AHA with the quaternary amine methenamine, which is an antibacterial, may also be considered. The advantage to methenamine is that bacteria do not develop a resistance to the drug, because the active form of the drug is formaldehyde (Krebs et al., 1984). Studies have also shown that the presence of AHA increases the antibacterial activity of the methenamine (Musher et al., 1976).

It should be understood that the examples and embodiments described herein are for illustrative purposes only and that various modifications or changes in light thereof will be suggested to persons skilled in the art and are to be included within the spirit and purview of this application and the scope of the appended claims.

References

Batich, C., J. Yan, M. Elsabee, C. Bucaria (1993) *Macromolecules* 126:4675–4681.

Brannon-Peppas, L., N. A. Peppas (1989) "Solute and Penetrant Diffusion in Swellable Polymers. IX. The Mechanisms of Drug Release from pH-Sensitive Swelling-Controlled Systems," *Journal of Controlled Release* 8:267.

Brannon-Peppas, L., N. A. Peppas (1990) "Dynamic and Equilibrium Swelling Behavior of pH-Sensitive Hydrogels Containing 2-Hydroxyethyl Methacrylate," *Biomaterials* 11:635.

Brazzini, A., W. R. Castaneda-Zuniga, C. C. Coleman, J. Hulbert, F. Castaneda, P. K. Reddy, D. W. Hunter, M. Darcy, T. Smith, K. Amplatz (1987) "Urostent Designs," *Seminars in Interventional Radiolog),* 4:26.

Breitenbach, H. M., R. P. Hausinger (1988) "*Proteus mirabilis* Urease Partial Purification and Inhibition by Boric Acid and Boronic Acids," *Biochem J.* 250:917.

Bronstedt, H., J. Kopecek (1991) "Hydrogels for Site-Specific Oral Drug Delivery: Synthesis and Characterization," *Biomaterials* 12:584.

Chien, Y. W. (1992) *Novel Drug Delivery Systems,* Marcel Dekker, Inc., New York. DeMoor, C. P., L. Doh, R. A. Siegel (1991) "Long-Term Structural Changes in pH-Sensitive Hydrogels," *Biomaterials* 12:836.

Eckstein, E. C., L. Pinchuk, M. R. Van De Mark (1983) "A Responsive Hydrogel Surface as a Means of Preventing Calcification in the Urinary Tract," *Polymer Preprints* 24:58.

Fowler, J. E. (1989) *Urinary Tract Infection and Inflammation,* Year Book Medical Publishers, Inc., Chicago.

Franco, G., C. DeDominicis, S. Dal Forno, F. Iori, C. Laurenti (1990) "The Incidence of Post-Operative Urinary Tract Infection in Patients with Ureteral Stents," *British Journal of Urology* 65:10.

Fuchs, O. (1989) *Polymer Handbook,* John Wiley and Sons, Inc., N.Y.

Greenley, R. C. (1989) *Polymer Handbook,* John Wiley and Sons, Inc.

Griffith, D. P., S. Bragin, D. M. Musher (1976) "Dissolution of Struvite Urinary Stones: Experimental Studies in Vitro," *Investigative Urology* 13:351.

Griffith, D. P., F. Khonsari, J. H. Skurnick, K. E. James, and Veterans Administration Cooperative Study Group (1988) "A Randomized Trial of Acetohydroxamic Acid for the Treatment and Prevention of Infection-Induced Urinary Stones in Spinal Cord Injury Patients," Journal of Urology 140:318.

Hukins, D. W .L., R. L. Hackett (1983) "Catheter Encrustation by Struvite," *British Journal of Urology* 55:304.

Izumi, K., T. Kunihiko, Published European Patent Application No. EP 0 065 884, published Dec. 1, 1982.

Kim, C., P. I. Lee (1992a) "Constant-Rate Drug Release from Novel Anionic Gel Beads with Transient Composite Structure," *Proceed. Intern. Symp. Control. Rel. Bioact. Mater.* 19:162.

Kim, C., P. I. Lee (1992b) "Hydrophobic Anionic Gel Beads for Swelling-Controlled Delivery," *Pharmaceutical Research* 9: 195.

Korsmeyer, R. W., N. A. Peppas (1984) "Solute and Penetrant Diffusion in Swellable Polymers. III. Drug Release from Glassy Poly(HEMA-co-NVP) Copolymers," *Journal of Controlled Release* 1:89.

Kou, J. H., G. L. Amidon, P. I. Lee (1988) "pH-Dependent Swelling and Solute Diffusion Characteristics of Poly(Hydroxyethyl Methacrylate-CO-Methacrylic Acid) Hydrogels," *Pharmaceutical Research* 5:592.

Krebs, M., R. B. Halvorsen, I. J. Fishman, N. Santos-Mendoza (1984) "Prevention of Urinary Tract Infection During Intermittent Catheterization," Journal of Urology 131:82.

Kunin, C. M. (1987) *Detection, Prevention, and Management of Urinary Tract Infections,* Lea and Febiger, Philadelphia.

Lee, P. I. (1988) *Controlled Release Systems: Fabrication Technology,* CRC Press, Inc., Boca Raton.

Liedberg, H., T. Lundeberg, P. Ekman (1990) "Refinements in the Coating of Urethral Catheters Reduces the Incidence of Catheter-Associated Bacteriuria," *Eur. Urol.* 17:236.

Mardis, H. K., R. M. Kroeger (1988) "Ureteral Stents," *Urologic Clinics of North America* 15:471.

McLean, R. J. C., J. Downey, L. Clapham, J. C. Nickel (1990) "Influence of Chondroitin Sulfate, Heparin Sulfate, and Citrate on *Proteus mirabilis*-Induced Struvite Crystallization in Vitro," *Journal of Urology* 144:1267.

McLean, R. J. C., J. Downey, L. Clapham, J. W. L. Wilson, J. C. Nickel (1991) "Pyrophosphate Inhibition of *Proteus mirabilis-Induced Struvite Crystallization in Vitro,"* *Clinica Chimica Acta* 200:107.

Mueller, K. F. (1987) "Release and Delayed Release of Water-Soluble Drugs from Polymer Beads with Low Water Swelling," In *Controlled-Release Technology Pharmaceutical Applications,* American Chemical Society, Washington, D.C.

Musher, D. M., D. P. Griffith, G. B. Templeton (1976) "Further Observations on the Potentiation of the Antibacterial Effect of Methenamine by Acetohydroxamin Acid," *Journal of Infectious Diseases* 133:564.

Nickel, J. C., J. Downey, J. W. Costerson (1992) "Movement of *Pseudomonas aeruginosa* Along Catheter Surfaces: A Mechanism in Pathogenesis of Catheter-Associated Infection," *Urology* 39:93.

Odian, G. (1981) *Principles of Polymerization,* John Wiley and Sons, New York. Olson, M. E., J. C. Nickel, J. W. Costerson (1989) "Animal Model of Human Disease Infection-Induced Struvite Urolithiasis in Rats," *American Journal of Pathology* 135:581.

Park, K. (1988) "Enzyme-Digestible Swelling Hydrogels as Platforms for Long-Term Oral Drug Delivery: Synthesis and Characterization," *Biomaterials* 9:435.

Pearce, R. S. C., L. R. West, G. T. Rodeheaver, R. F. Edlich (1984) "Evaluation of a New Hydrogel Coating for Drainage Tubes," *American Journal of Surgery* 148:687.

Pepper, K. et al. (1952) *J. Chem. Soc.* 3129.

Ramsay, J. W. A., R. A. Miller, P. R. Crocker, B. J. Ringrose, S. Jones, D. A. Levison, H. N. Whitfield, J. E. A. Wickham (1986) "An Experimental Study of Hydrophilic Plastics for Urological Use," *British Journal of Urology* 58:70.

Reid, G., C. Tieszer, R. Foerch, H. J. Busscher, A. E. Khoury, A. W. Bruce (1993) "Adsorption of ciprofloxacin to urinary catheters and effect on subsequent bacterial adhesion and survival," *Colloids and Surfaces B: Biointerfaces* 1:9-16.

Ritger, P. L., N. A. Peppas (1987) "A Simple Equation for Description of Solute Release II. Fickian and Anomalous Release from Swellable Devices," *Journal of Controlled Release* 5:37.

Robert, C. C. R., P. A. Buri, N. A. Peppas (1987) "Influence of the Drug Solubility and Dissolution Medium on the Release from Poly(2-Hydroxyethyl Methacrylate) Microspheres," *Journal of Controlled Release* 5:151.

Saunders, K. (1988) *Organic Chemistry of Polymers—*2nd ed., Chapman and Hall Pub., New York.

Soloman, D. D., R. J. Sheretz (1987) "Antibiotic Releasing Polymers," *Journal of Controlled Release* 6:343.

Soloman, D. D., U.S. Pat. No. 4,999,210, issued Mar. 12, 1991.

Soriano, F., C. Ponte, M. Santamaria, R. Fernandez-Roblas (1987) "Struvite Crystal Formation by *Corynebacterium* Group D2 in Human Urine and Its Prevention by Acetohydroxamic Acid," *Eur. Urol.* 13:271.

Stamm, W. E. (1991) "Catheter-Associated Urinary Tract Infections: Epidemiology, Pathogenesis, and Prevention," *American Journal of Medicine* 91:3B-65S.

Swartz, R., J. Messana, C. Holmes, J. Williams (1991) "Biofilm Formation on Peritoneal Catheters Does Not Require the Presence of Infection," *Trans. Am. Soc. Artifi. Intern. Organs* 37:626.

Takeuchi, H., K. Kobashi, O. Yoshida (1980) "Prevention of Infected Urinary Stones in Rats by Urease Inhibitor: A New Hydroxamic Acid Derivative," *Investigative Urology* 18:102.

Tarcha, P. J. (1991) *Polymers for Controlled Delivery,* CRC Press, Boca Raton.

Whitbourne, R. J., M. A. Mangan, Published European Patent Application EP 0 426 486, published May 8, 1991.

Wu, K. J., X. Q. Li, S. J. Yao (1985) "Induction and Inhibition of Struvite Bladder Stones in Rats," *Urolithiasis and Related Clinical Research* [Proceedings of the Fifth International Symposium]:957.

We claim:

1. A method for controlling a bacterial infection associated with the use of an indwelling medical device in an environment which is desired to be kept free of bacterial infection, wherein said infection would cause an increase in the pH of the environment of said indwelling medical device, wherein said method comprises:

implanting into a patient in need of such a medical device an indwelling medical device which is coated with a biologically active agent integally incorporated throughout and trapped within a pH-sensitive polymer matrix, wherein said polymer matrix swells to release said agent at an increased rate or only upon said change of pH, thereby controlling said infection.

2. The method, according to claim 1, further comprising selecting said medical device from the group consisting of ureteral or urethral catheters or stents, heart valves, pacemakers, artificial joints, gastrointestinal tubes, intrauterine devices, and diaphragms.

3. The method, according to claim 2, further comprising selecting said environment to be urine and wherein said change in pH is to a pH which is greater than about 8.5.

4. An indwelling medical device which controls bacterial infection which causes an increase in the pH of the environment of the medical device, wherein said indwelling medical device comprises a means for inhibiting growth of bacteria which would cause said increase in pH in the environment surrounding said indwelling medical device in the absence of said means for inhibiting said growth of bacteria, wherein said means comprises a biologically active agent integrally incorporated throughout and trapped within a pH-sensitive polymer matrix coating of said indwelling device such that said agent is released from said pH-sensitive polymer matrix at an increased rate or only upon an increase in pH of the environment of the indwelling medical device above about pH 7.4 due to the commencement of bacterial growth within the environment of said indwelling medical device, wherein said increase in pH causes said pH-sensitive polymer matrix to swell to release said biologically active agent trapped within said pH-sensitive polymer matrix.

5. The device, according to claim 4, wherein said pH-sensitive polymer matrix comprises a weakly acidic monomer.

6. The device, according to claim 5, wherein said weakly acidic monomer is selected from the group consisting of methacrylic acid and acrylic acid.

7. The device, according to claim 5, wherein said pH-sensitive polymer further comprises a hydrophobic monomer selected from the group consisting of butylmethyl acrylate and methyl methacrylate.

8. The device, according to claim 4, which is a catheter or stent.

* * * * *

UNITED STATES PATENT AND TRADEMARK OFFICE
CERTIFICATE OF CORRECTION

PATENT NO. : 5,554,147

DATED : September 10, 1996

INVENTOR(S) : Christopher D. Batich, Marc S. Cohen, and Kirk Foster

It is certified that error appears in the above-identified patent and that said Letters Patent is hereby corrected as shown below:

Column 1: Lines 57-58: "Obstruction of the temperatures the placement of a ureteral stent" should read --Obstruction of the ureter requires the placement of a ureteral stent--.
Column 2: Line 60: "grease" should read --urease--.
Column 3: Line 1: "hahibition" should read --inhibition--.
Column 9: Lines 25-26: "MMA-JAA" should read --MMA/AA--; Line 58: "fists" should read --lists--.
Column 12: Line 19: "wash,ed" should read --washed--; Line 25: "swelling. (Robert et al., 1987)." should read --swelling (Robert et al., 1987).--.
Column 13: Line 20: "absorbantes" should read --absorbances--; Line 25: "contrast, to" should read --contrast to--.
Column 16: Line 32: "Radiolog)," should read --Radiology--.
Column 17: Line 7: "Syrup." should read --Symp.--.
Column 18: Line 37: "Artifi." should read --Artif.--.

Signed and Sealed this

Twenty-second Day of April, 1997

Attest:

BRUCE LEHMAN

*Attesting Officer*     Commissioner of Patents and Trademarks